(12) United States Patent
Zohar et al.

(10) Patent No.: US 12,015,638 B1
(45) Date of Patent: Jun. 18, 2024

(54) COMPUTING SYSTEM FOR CROSS-SITE REQUEST FORGERY ATTACK PROTECTION

(71) Applicant: Allscripts Software, LLC, Raleigh, NC (US)

(72) Inventors: Haggai Zohar, Omer (IL); Oren Dvash, Omer (IL)

(73) Assignee: ALTERA DIGITAL HEALTH INC., Niagara Falls, NY (US)

( * ) Notice: Subject to any disclaimer, the term of this patent is extended or adjusted under 35 U.S.C. 154(b) by 787 days.

(21) Appl. No.: 16/591,699

(22) Filed: Oct. 3, 2019

(51) Int. Cl.
| | |
|---|---|
| H04L 9/40 | (2022.01) |
| G16H 10/60 | (2018.01) |
| H04L 67/01 | (2022.01) |
| H04L 67/10 | (2022.01) |
| H04L 67/53 | (2022.01) |

(52) U.S. Cl.
CPC ......... H04L 63/1483 (2013.01); G16H 10/60 (2018.01); H04L 63/0853 (2013.01); H04L 67/01 (2022.05); H04L 67/10 (2013.01); H04L 67/53 (2022.05)

(58) Field of Classification Search
CPC ......... H04L 51/32; H04L 67/22; H04L 67/24; G06F 19/322; G06Q 2220/10
See application file for complete search history.

(56) References Cited

U.S. PATENT DOCUMENTS

| | | | |
|---|---|---|---|
| 8,020,193 B2 | 9/2011 | Bhola et al. | |
| 8,495,137 B2 | 7/2013 | Amit et al. | |
| 8,775,818 B2 | 7/2014 | Schneider | |
| 8,850,219 B2 | 9/2014 | Dapkus et al. | |
| 8,924,553 B2 | 12/2014 | Schneider | |
| 9,021,586 B2 | 4/2015 | Garskof | |
| 9,118,619 B2 | 8/2015 | Gantman et al. | |
| 2012/0023377 A1* | 1/2012 | Garskof | G06F 16/9566 714/48 |
| 2014/0189808 A1* | 7/2014 | Mahaffey | H04L 63/083 726/4 |
| 2014/0325499 A1* | 10/2014 | Jawa | G06F 8/65 717/171 |
| 2015/0213195 A1* | 7/2015 | Blechman | G16H 10/60 705/51 |

(Continued)

*Primary Examiner* — Mahran Y Abu Roumi
(74) *Attorney, Agent, or Firm* — CALFEE, HALTER & GRISWOLD LLP (57) ABSTRACT

A server agent application receives a uniform resource locator (URL) from a client agent application, the URL including an identifier for a graphical resource. The server agent application determines, based upon the URL, that a third-party application is to provide the graphical resource. The server agent application causes an intermediate application to be launched. The intermediate application requests a webpage from the third-party application, the webpage including a security token for a user session between the client agent application and the third-party application. The intermediate application receives the webpage and constructs a modified URL based upon the URL and the security token included in the webpage. The intermediate application transmits the modified URL to the third-party application, wherein the third-party application causes the client agent application to receive the graphical resource based upon the modified URL.

19 Claims, 6 Drawing Sheets

(56) References Cited

U.S. PATENT DOCUMENTS

| | | | | |
|---|---|---|---|---|
| 2017/0180302 A1* | 6/2017 | Tseng | ................... | G06Q 10/10 |
| 2018/0203674 A1* | 7/2018 | Dayanandan | ............. | G06F 8/35 |
| 2018/0295134 A1* | 10/2018 | Gupta | ................... | H04L 67/02 |

* cited by examiner

COMPUTING SYSTEM FOR CROSS-SITE REQUEST FORGERY ATTACK PROTECTION

BACKGROUND

Electronic health records applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient record maintained by an EHR to relatively quickly ascertain problems being experienced by the patient, medications currently being taken by the patient, and so forth.

Agent applications are computer-executable applications that are also configured to assist healthcare workers with providing care to patients. However, unlike EHRs, which access patient data from an electronic source (e.g., a database of the EHR) under control of a single healthcare organization, agent applications are configured to access (and optionally store) patient data from a plurality of electronic sources that may be under control of different healthcare organizations. For instance, the plurality of electronic sources may include different EHRs, health information exchanges (HIEs), and so forth.

In certain cases, agent applications may interface with third-party applications (applications other than EHRs). In an example, an agent application may interface with a third-party application in order to present graphical resources on a display of a computing device that executes the agent application. More specifically, in the example, the agent application may be provided with computer-executable code that, when executed by a processor, causes graphical user interface (GUI) features from the third-party application, wherein a GUI presented by the agent application on a display comprises such GUI features. The GUI of the agent application may further include data that is aggregated from a plurality of electronic sources together with the GUI features referenced above.

An agent application that interfaces with a third-party application may leave the agent application and/or the third-party application vulnerable to a cross-site request forgery (CSRF) attack. A CSRF attack is a type of security exploit of a website where unauthorized commands are transmitted from a computing device that the website trusts. CSRF attacks exploit trust that the website has with respect to a browser executing on the computing device.

One conventional approach for protecting against CSRF attacks is to include a security token (e.g., a random number or a pseudo-random number) in requests that are passed between a client-side application and a server-side application. However, this conventional approach is based upon the presumption that a user of the client-side application is trustworthy and/or that a client computing device that executes the client-side application has not been compromised. For certain types of applications, including agent applications that can be employed to access data of numerous patients, it is undesirable to make such presumption. In an example, the third-party application referenced above may have CSRF prevention enabled, and therefore may transmit a security token to the agent application. When the agent application transmits a request to the third-party application, the request includes the security token. A malicious end user may acquire the security token and make a request for data that the end user should not be able to see (e.g., clinical data of a patient that the end user is desirably prevented from viewing); as the request includes the security token, however, the third party application may respond to the request, allowing the end user to acquire data that the end user is not authorized to acquire.

SUMMARY

The following is a brief summary of subject matter that is described in greater detail herein. This summary is not intended to be limiting as to the scope of the claims.

Described herein are various technologies pertaining to protection against cross-site request forgery (CSRF) attacks. More specifically, an intermediate application is described herein that acts as an intermediary between a client agent application and a third-party application. The intermediate application enables a third-party application to provide a graphical resource to the client agent application without exposing a security token to the client agent application, the security token being required by the third-party application.

In operation, a client agent application authenticates with a third-party application, thereby causing the third-party application to generate a security token. The client application receives a selection of a graphical object shown on a display. The graphical object is assigned to a graphical resource that is to be provided to the client agent application by the third-party application. In an example, the graphical object may be a link or an icon that is displayed within a GUI for the client agent application. Responsive to receiving the selection of the link, the client agent application constructs a uniform resource locator (URL) and transmits the URL to a server agent application. The URL includes an identifier for the graphical resource. The server agent application receives the URL from the client agent application. The server agent application determines, based upon the URL, that the graphical resource is to be provided by the third-party application. Responsive to determining that the graphical resource is to be provided by the third-party application, the server agent application causes an intermediate application to be launched.

The server agent application causes the URL to be provided to the intermediate application. Responsive to being provided with the URL, the intermediate application requests a webpage from the third-party application. The webpage includes the security token for the user session with the user that was previously generated when the client agent application authenticated with the third-party application. The intermediate application parses the webpage to extract the security token from the webpage. The intermediate application then constructs a modified URL based upon the URL and the security token. More specifically, the modified URL includes the identifier for the graphical resource and security token. The intermediate application transmits the modified URL to the third-party application.

The third-party application authenticates the user based upon the security token included in the modified URL. Responsive to authenticating the user, the third-party application generates the graphical resource based upon the modified URL. The intermediate application performs processing on the graphical resource. For instance, the intermediate application removes the security token from the graphical resource if the security token is included in the graphical resource. The intermediate application transmits the graphical resource to the client agent application.

Responsive to transmitting the graphical resource to the client agent application, the intermediate application may cause itself to cease executing. Responsive to receiving the graphical resource from the intermediate application, the client agent application presents the graphical resource on the display.

The above-described technologies present various advantages over conventional approaches to preventing CSRF attacks. First, the intermediate application described above enables a graphical resource to be provided by a third-party application to a client agent application without exposing a security token to the client agent application. Second, unlike conventional approaches, the above-described technologies reduce use of computing resources of the client agent application, as the client agent application does not need to be configured to perform additional processing to protect against CSRF attacks.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to cross-site request forgery (CSRF) attack protection are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component," "application," and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Figure 1:
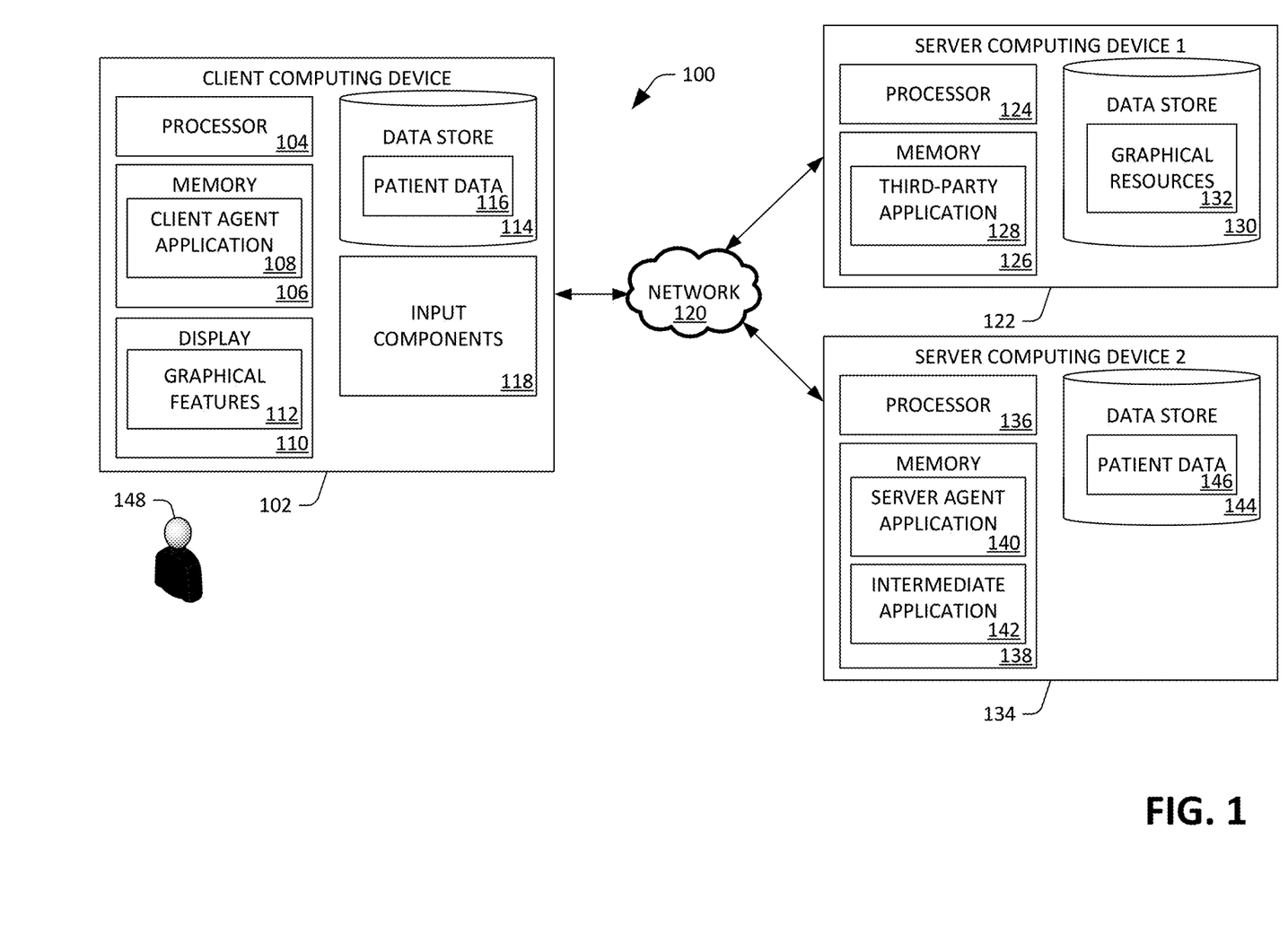
FIG. 1 is a functional block diagram of an exemplary computing system that facilitates cross-site request forgery (CSRF) attack protection.

With reference to FIG. 1, an exemplary computing system 100 that facilitates CSRF attack protection is illustrated. The computing system 100 includes a client computing device 102 that is operated by a user 148 (e.g., a healthcare worker). In an example, the client computing device 102 may be a desktop computing device, a laptop computing device, a tablet computing device, a smartphone, or a wearable computing device, such as a smartwatch.

The client computing device 102 comprises a processor 104 and memory 106, wherein the memory 106 has a client agent application 108 loaded therein. In general, the client agent application 108 (when executed by the processor 104) is configured to retrieve and display patient data for a patient (or patient data for a plurality of patients) that is aggregated from a plurality of electronic sources. In an example, the plurality of electronic sources may include different electronic health record (EHR) applications, different Health Information Exchanges (HIEs), and/or third-party applications. In contrast, an EHR application is configured to only retrieve and display patient data from an electronic source (e.g., an EHR database) that is maintained by the EHR application. In an embodiment, the client agent application 108 may be executed within a web browser that is executed by the processor 104 of the client computing device 102.

The client computing device 102 further comprises a display 110, whereupon graphical features 112 may be presented thereon. For instance, a graphical user interface (GUI) for the client agent application 108 may be displayed on the display 110 as part of the graphical features 112. In an embodiment, the display 110 may be a touchscreen display.

The client computing device 102 further comprises a data store 114. The data store 114 may store patient data 116 for patients. The patient data 116 may overlap in part or wholly with patient data (described below) maintained by a server agent application (also described below).

The client computing device 102 additionally comprises input components 118 that enable the client computing device 102 to receive input from the user 148. In an example, the input components 118 may include a mouse, a keyboard, a touchscreen, a scroll wheel, a trackpad, a microphone, a camera, and/or a video camera.

The computing system 100 further comprises a first server computing device 122 that is in communication with the client computing device 102 by way of a network 120 (e.g., the Internet, intranet, etc.). The first server computing device 122 comprises a processor 124 and memory 126, wherein the memory 126 has a third-party application 128 loaded therein. In general, the third-party application 128 (when executed by the processor 124) is configured to maintain graphical resources (described below) that are to be provided to the client agent application 108.

In an embodiment, the third-party application 128 may be a business intelligence application that provides reporting, analysis, and monitoring functionality (via the graphical resources). More specifically, the business intelligence application may provide scorecard and dashboard functionality, enterprise reporting functionality, online analytical processing (OLAP) functionality, and alert and proactive notification functionality.

The first server computing device 122 further comprises a data store 130 that stores graphical resources 132 that are to be provided to the client agent application 108 (or another client agent application). In an embodiment, a graphical resource in the graphical resources may be a GUI. In the embodiment, after the third-party application 128 has provided the GUI to the client agent application 108, the client agent application 108 may cause the GUI to be populated with patient data for a patient (or patient data for a plurality of patients) that is provided to the client agent application 108 by a server agent application (described below). Thus, the graphical resources 132 may correspond to "views" of the client agent application 108. In an example, a view may be an analytics dashboard.

The computing system 100 further comprises a second server computing device 134. The second server computing device 134 is in communication with the client computing device 102 by way of the network 120 (or another network). The second server computing device 134 is also in in communication with the first server computing device 122 by way of the network 120 (or another network).

The second server computing device 134 comprises a processor 136 and memory 138, wherein the memory 138 has a server agent application 140 and an intermediate application 142 loaded therein. In general, the server agent application 140 (when executed by the processor 136) is configured to retrieve patient data from a plurality of electronic sources (as opposed to patient data from a single electronic source) and to provide the patient data to the client agent application 108 for display on the display 110 as part of the graphical features 112. Thus, the server agent application 140 and the client agent application 108 form a distributed application with both server-side and client-side functionality, collectively referred to herein as "an agent application." As will be described in greater detail below, the intermediate application 142 (when executed by the processor 136) is configured to protect against CSRF attacks.

The second server computing device 134 further comprises a data store 144 that stores patient data 146 for patients. The patient data 146 may include electronic health records, prescription records, claims data, patient/disease registries, health surveys data, clinical trials data, etc. As noted above, the patient data 146 is aggregated from a plurality of electronic sources (e.g., different EHR applications, different HIEs, etc.).

Figure 2:
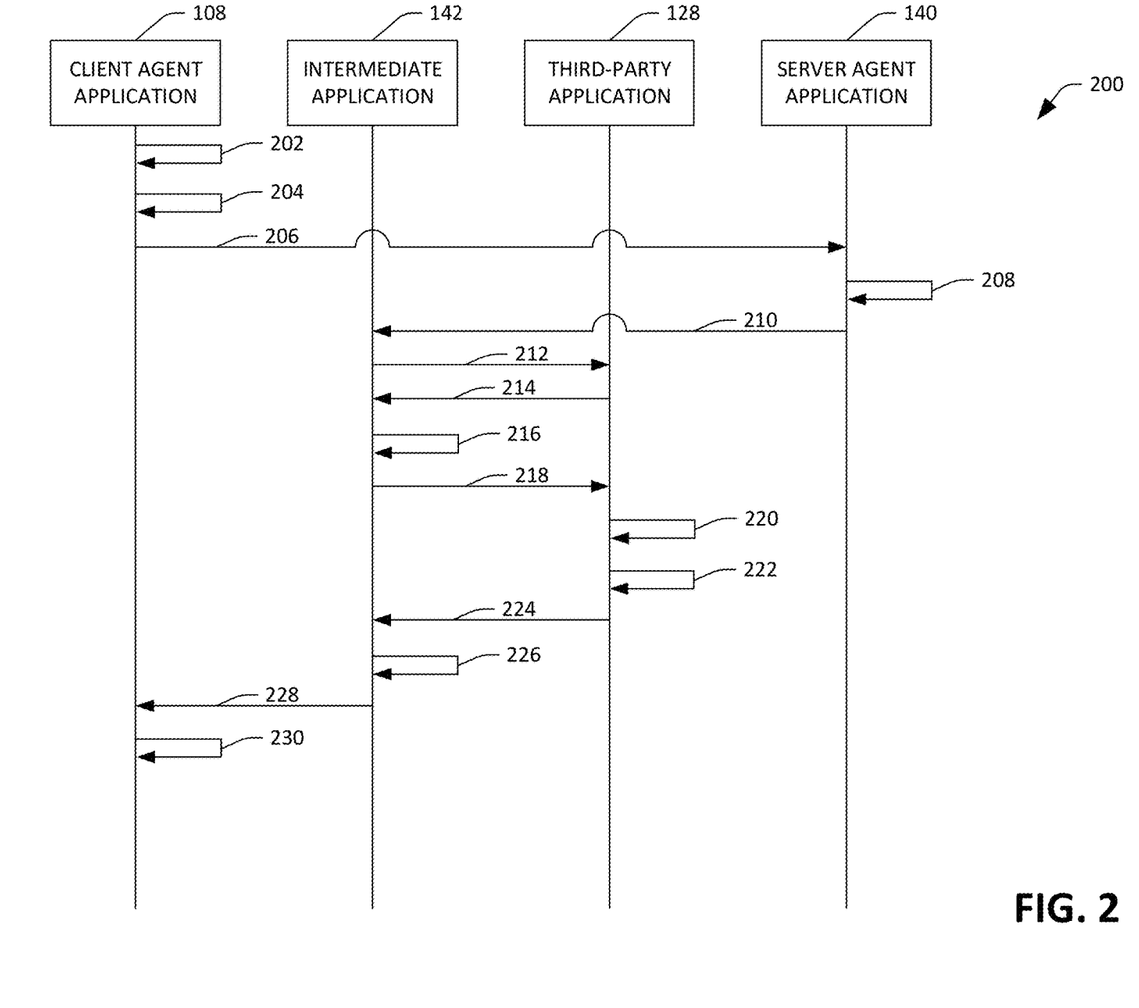
FIG. 2 is a control flow diagram that illustrates operation of the computing system in FIG. 1.

Turning now to FIG. 2, a control flow diagram 200 is illustrated that describes operation of the computing system 100. Prior to step 202, it is contemplated that the third-party application 128 has generated a security token for a user session with the user 148. More specifically, the client agent application 108 receives credentials for the user 148 as input from the user 148. The client agent application 108 transmits the credentials for the user 148 to the third-party application 128. The client agent application 108 may transmit the credentials directly to the third-party application 128, or the client application 108 may transmit the credentials to the server agent application 140, which may then forward the credentials to the third-party application 128. The third-party application 128 authenticates the user 148 based upon the credentials for the user 148. For instance, the third-party application 128 may authenticate the user 148 based upon a comparison between the credentials for the user 148 and stored credentials for the user 148 (not shown in FIG. 1). Responsive to authenticating the user 148, the third-party application 128 generates the security token for the user session with the user 148. In an embodiment, the security token may be a random number or a pseudo-random number. Although the third-party application 130 has been described as authenticating the user 148, it is to be understood that authentication of the user 148 may be performed by another application (not shown) executing on the first server computing device 124 or on another server computing device.

At step 202, the client agent application 108 receives a selection of a graphical object by the user 148 (via the input components 118), the graphical object being shown on the display 110. The graphical object is assigned to a graphical resource in the graphical resources 132. In an example, the graphical object may be a link or an icon that is displayed within a GUI for the client agent application 108.

At step 204, responsive to receiving the selection of the link, the client agent application 108 constructs a uniform resource locator (URL). The URL includes an identifier for the graphical resource. In an example where the graphical resource is a target view and the graphical object assigned to the graphical resource is displayed in a source view, the URL includes an identifier for the source view and an identifier for the target view. At step 206, the client agent application 108 transmits the URL to the server agent application 140.

The server agent application 140 receives the URL from the client agent application 108, and at step 208, the server agent application 140 determines, based upon the URL, that the graphical resource is to be provided by the third-party application 128. Responsive to determining that the graphical resource is to be provided by the third-party application 128, the server agent application 140 causes the intermediate application 142 to be launched on the second server computing device 134.

Example code of the intermediate application 142 that performs at least some of the functionality that is to be described below is illustrated below:

```
<!DOCTYPE html PUBLIC "-//W3C//DTD XEITML 1.0
    Transitional//EN"
"http://www.w3.org/TR/xhtml1/DTD/xhtml1-transition-
    al.dtd">
<html xmlns="http://www.w3.org/1999/xhtml">
<head>
<meta                    http-equiv="X-UA-Compatible"
    content="IE=edge"/>
<title>MSSP Patient List</title>
<script src="../javascript/jquery/jquery-3.3.1.min.js"></
    script>
<script language="javascript" type="text/javascript">
var validateRandNum;
$.ajax({
    url:
'http://$_NODE_ANALYTICS_WEB_SERVER_
    NAMES/MicroStrategy/asp/Main.a spx',
    async: false,
    type: 'GET',
        success: function(res) {
            var     temp=res.substring(res.indexOf("vali-
                dateRandNum"), res.length);
```

```
        validateRandNum=temp.substring(temp.indexOf
            ("'")+1, temp.indexOf(";") -1);
    }
});
function closeWindow( ) {
window.open(", '_self',").focus( );
window.close( );
}
</script>
</head>
<body
onload="window.open(http://$_NODE_ANALYT-
    ICS_WEB_SERVER_NAME$/Mi    croStrategy/asp/
    Main.aspx?Port=0&evt=3140&src=Main.aspx.3140&
    validateRandN         um='+validateRandNum+
    '&documentID=DC7F45594558C4C74C35059E9763
    4C44
    ¤tViewMedia=1&Port=0&share=1&visMode=
    1&elementsPromptAnswers=2
    A039F1F4CA09F511A578E98C22B1902;
    2A039F1F4CA09F511A578E98C22B1902:
    <%=Request. Query String("monthid")%>:<%=Re-
    quest.QueryString("monthdesc")
    %>,37F251AB488F6D88F7E30FB09E2A479D;
    37F251AB488F6D88F7E30FB09E2 A479D:<%=Re-
    quest.QueryString("measureid")%>','resizable');win-
    dow.focus( );close Window( );pagename.focus( );">
</body>
</html>
```

At step 210, the server agent application 140 causes the URL to be provided to the intermediate application 142. At step 212, responsive to being provided with the URL, the intermediate application 142 requests a webpage from the third-party application 128. The webpage may be a "launch page" of the third-party application 128, that is, an introductory page of the third-party application 128 that is presented to the user 148 before the third-party application 128 performs its intended functionality. The webpage includes the security token for the user session with the user 148 that was generated previously. In an example, the security token may be included in Hypertext Markup Language (HTML) of the webpage. At step 214, responsive to receiving the request from the intermediate application 142, the third-party application 128 transmits the webpage to the intermediate application 142.

At step 216, the intermediate application 142 parses the webpage to extract the security token from the webpage. At step 218, the intermediate application 142 constructs a modified URL based upon the URL and the security token. More specifically, the modified URL includes the identifier for the graphical resource and security token. In an example where the graphical resource is the target view, the modified URL may include an identifier for the source view, an identifier for the target view, and the security token. At step 218, the intermediate application 142 transmits the modified URL to the third-party application 128.

At step 220, the third-party application 128 authenticates the user 148 based upon the security token included in the modified URL. At step 222, responsive to authenticating the user 148, the third-party application 128 generates the graphical resource based upon the modified URL. For instance, the third-party application 128 may retrieve the graphical resource from the graphical resources 132 based upon the modified URL. The third-party application 128 may also generate the graphical resource based upon other data. For instance, graphical resource is to include de-identified patient data, the third-party application 128 may retrieve patient data and generate the graphical resource based upon the patient data. In an embodiment, the graphical resource may be comprised wholly or in part by HTML code. At step 224, the third-party application 128 transmits the graphical resource to the intermediate application 142.

At step 226, the intermediate application 142 performs processing on the graphical resource. For instance, the intermediate application 142 removes the security token from the graphical resource if the security token is included in the graphical resource (e.g., as part of the HTML code). The intermediate application 142 may also remove content from the graphical resource. At step 228, the intermediate application 142 transmits the graphical resource to the client agent application 108. Responsive to transmitting the graphical resource to the client agent application 108, the intermediate application 142 may cause itself to cease execution on the second server computing device 134.

At step 230, responsive to receiving the graphical resource from the intermediate application 142, the client agent application 108 presents the graphical resource on the display 110 as part of the graphical features 142. In an example wherein the graphical resource is a target view and a GUI for the client agent application 108 is displaying a source view, the client agent application 108 may remove the source view from the display 110 and present the target view in place of the source view within the GUI for the client agent application 108.

In an embodiment, the graphical resource is a GUI for the client agent application 108 that is to be populated with patient data for a patient (or patient data for a plurality of patients) from the data store 144 of the second server computing device 134. As such, the client agent application 108 may transmit an identifier for a patient or a patient characteristic to the server agent application 140. Responsive to receiving the identifier for the patient or the patient characteristic, the server agent application 140 may execute a search over the patient data 146 based upon the identifier for the patient or the patient characteristic (e.g., patients belonging to a particular geographic area, patients having a similar health condition, etc.). The search produces search results, wherein the search results include patient data for the patient or patient data for a plurality of patients having the patient characteristic. The server agent application 140 transmits the patient data to the client agent application 108. The client agent application 108 then populates the GUI for the client agent application 108 with the patient data.

It is to be understood that some or all of the steps 202-230 in the control flow diagram 200 may be repeated for requests for different graphical resources that are maintained by the third-party application 128. For instance, the server agent application 140 may receive a second URL from the client agent application 108, the second URL including an identifier for a second graphical resource that is to be provided by the third-party application 128. The server agent application 108 may determine that the second graphical resource is to be provided by the third-party application 128 and the server agent application 108 may cause the intermediate application 142 to be launched. The intermediate application 142 may request a second webpage from the third-party application 128, the second webpage including the security token for the user. Responsive to receiving the second webpage from the third-party application 128, the intermediate application 142 extracts the security token from the second webpage. The intermediate application 142 constructs a second modified URL based upon the second URL and the security token, the second modified URL including the second URL and the security token. The intermediate application 142 transmits the second modified URL to the third-party application 128, wherein the third-party application 128 generates or retrieves the second graphical resource based upon the second modified URL and causes the second graphical resource to be presented on the display 110 of the client computing device 102.

Figure 3:
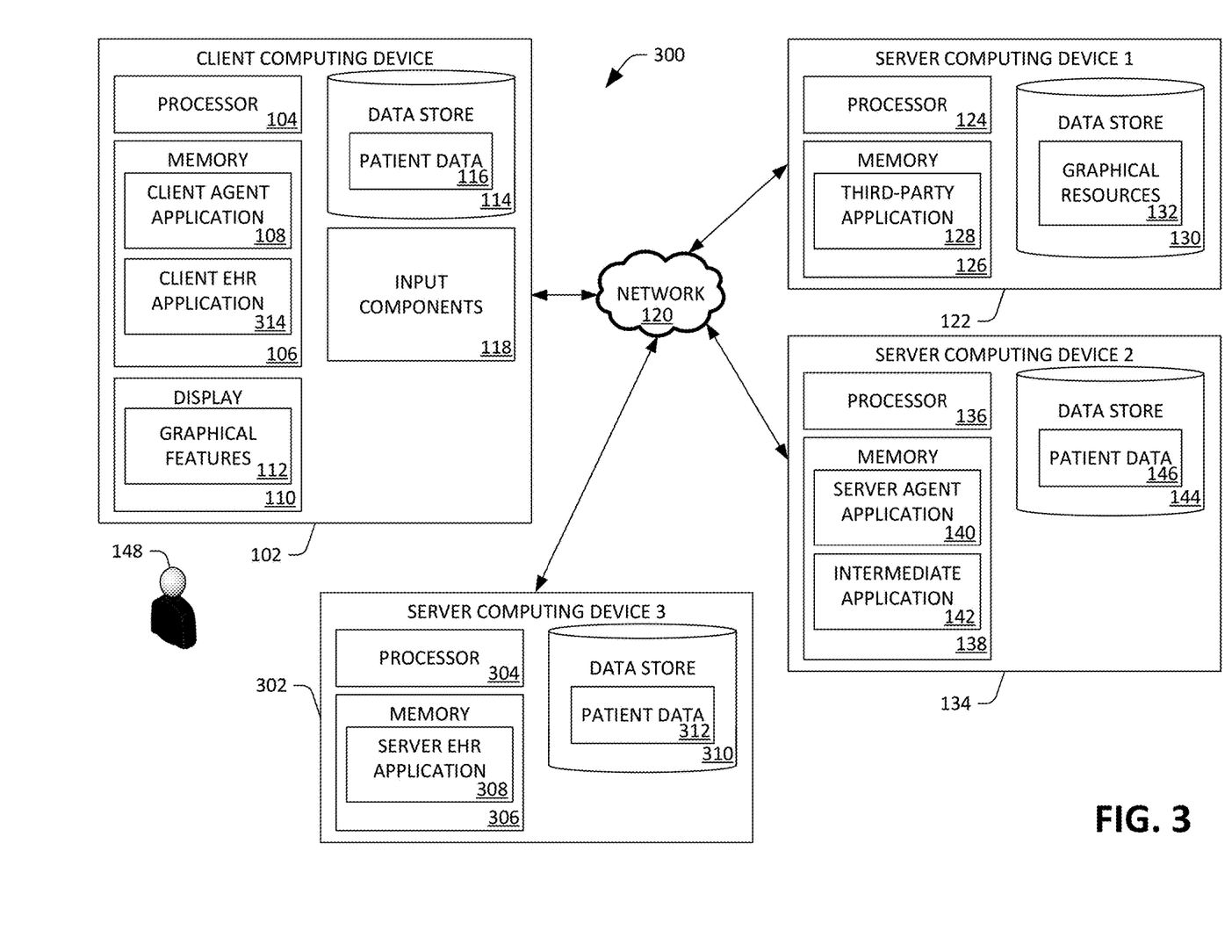
FIG. 3 is a functional block diagram of another exemplary computing system that facilitates CSRF attack protection.

Referring now to FIG. 3, an exemplary computing system 300 that facilitates CSRF protection is illustrated. The computing system 300 includes all of the components of the computing system 100 described above in the description of FIG. 1 (e.g., the client computing device 102, the first server computing device 122, the second server computing device 134, and so forth).

The computing system 300 further includes a third server computing device 302. The third server computing device 302 is in communication with the client computing device 102 by way of the network 120 (or another network). In an embodiment, the third server computing device 302 may be in communication with the second server computing device 134 by way of the network 120 (or another network).

The third server computing device 302 comprises a processor 304 and memory 306, wherein the memory 306 has a server EHR application 308 loaded therein. In general, the server EHR application 308 (when executed by the processor 304) is configured to perform a variety of programmatic tasks related to patient healthcare in a healthcare facility (e.g., patient intake, prescription generation, patient record creation and maintenance, etc.).

The third server computing device 302 further comprises a data store 310 that stores patient data 312 that is maintained by the server EHR application 308. The patient data 312 may include electronic health records, prescription records, claims data, patient/disease registries, health surveys data, clinical trials data, etc. However, in contrast to the patient data 146, the patient data 312 represents patient data maintained by the server EHR application 108 (i.e., patient data maintained by a single healthcare organization that utilizes the server EHR application 108).

In the computing system 300, the memory 106 of the client computing device 102 additionally has a client EHR application 314 loaded therein. In general, the client EHR application 314 (when executed by the processor 104) is configured to communicate with the server EHR application 308 in order to perform programmatic tasks related to patients in a healthcare facility.

The computing system 300 operates in a manner similar to that described above in the description of FIGS. 1 and 2. For instance, the computing system 300 may perform the steps 202-230 detailed above in the control flow diagram 200. However, in the computing system 300, the client computing device 102 executes the client agent application 108 concurrently with the client EHR application 314. In an example, the client computing device 102 may display a GUI for the client agent application 108 as an overlay to a GUI for the client EHR application 314 on the display 112. In another example, the client computing device 102 may display the GUI for the client agent application 108 side-by-side with the GUI for the client EHR application 314 on the display 112.

Figure 4:
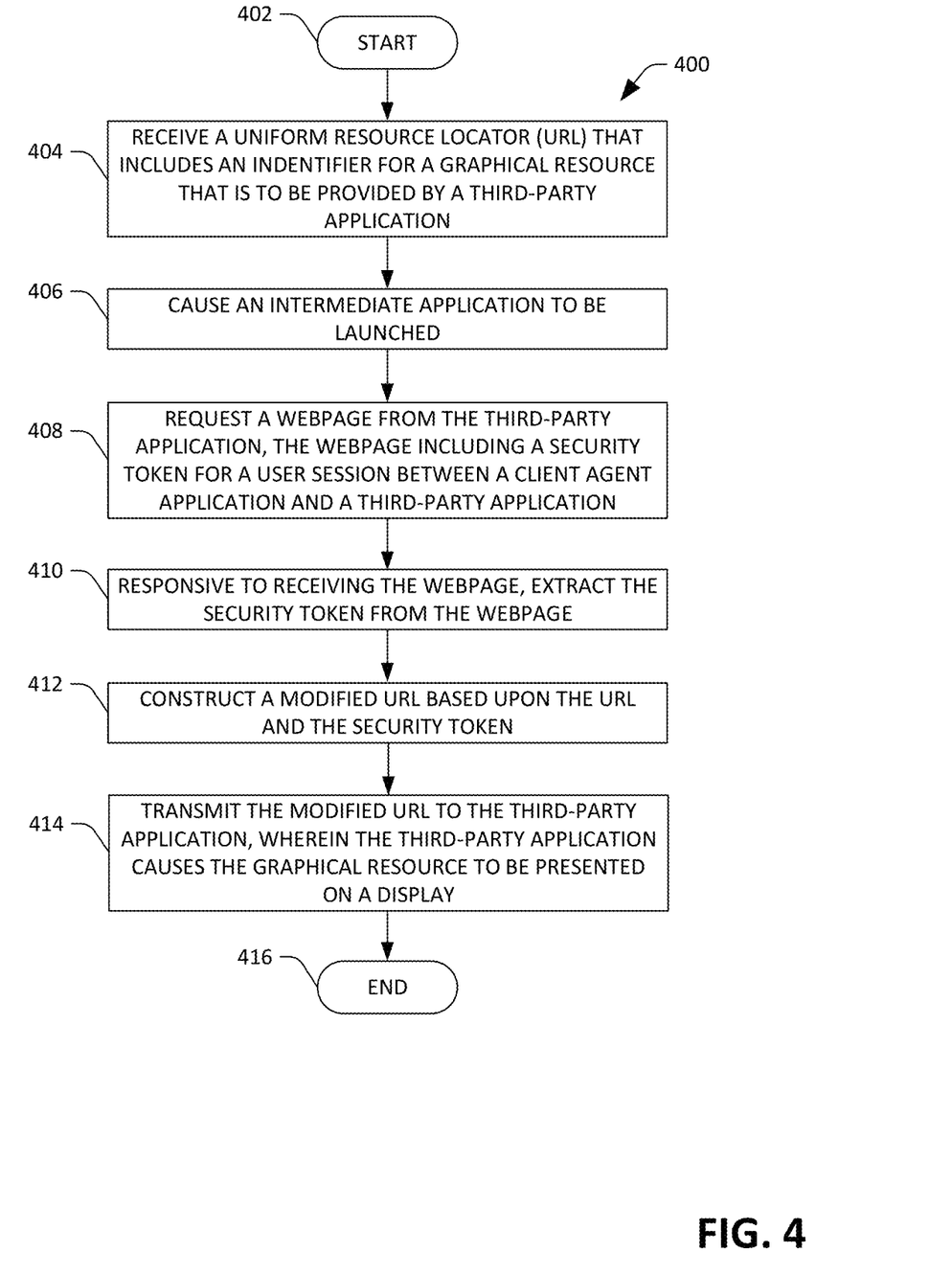
FIG. 4 is a flow diagram that illustrates an exemplary methodology performed by a client computing device that facilitates CSRF attack protection.
Figure 5:
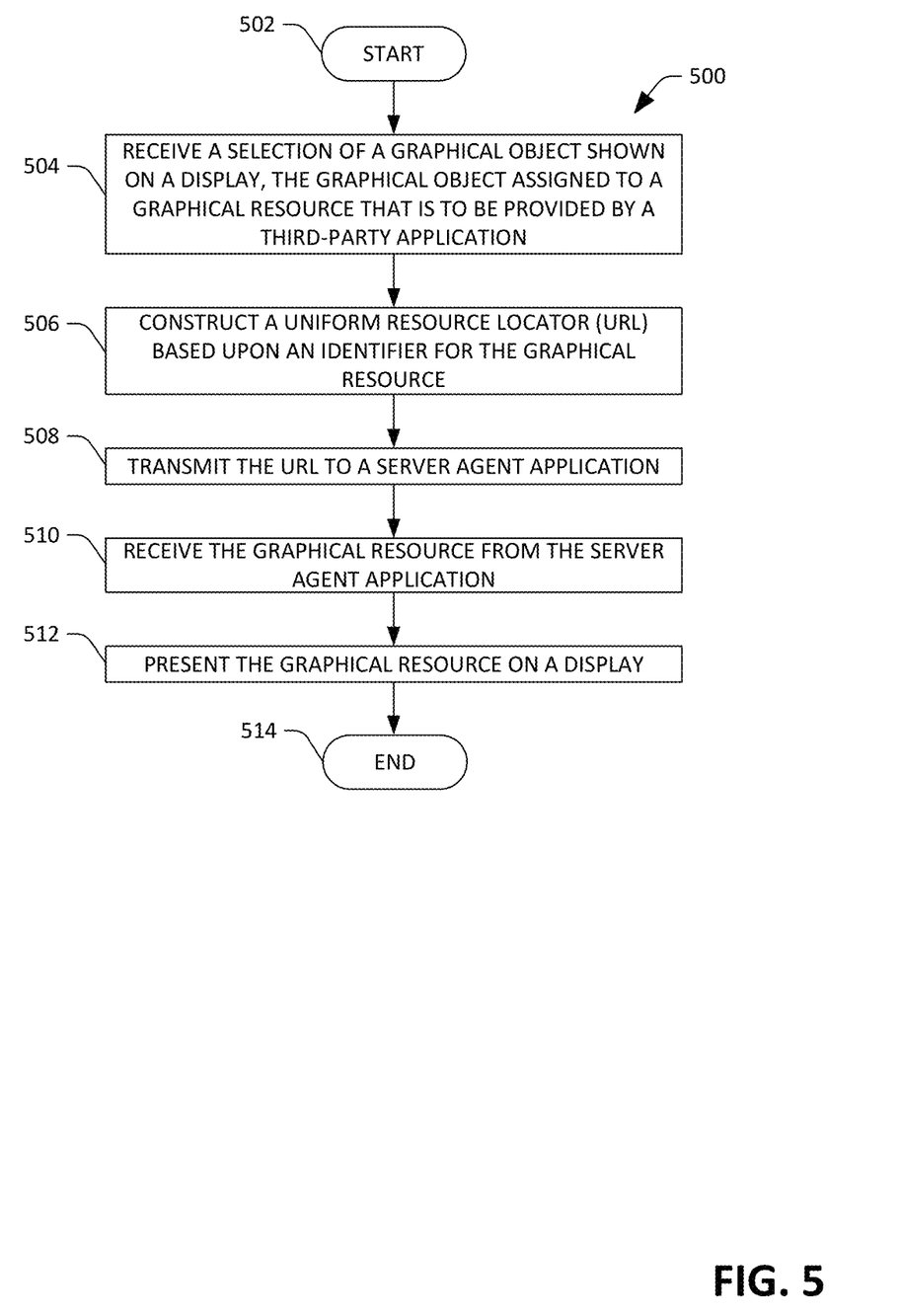
FIG. 5 is a flow diagram that illustrates an exemplary methodology executed by a third-party application that facilitates CSRF attack protection.

FIGS. 4 and 5 illustrate exemplary methodologies relating to CSRF attack protection. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 4, a methodology 400 performed by a server computing device that facilitates CSRF attack protection is illustrated. The methodology 400 begins at 402, and at 404, a server agent application being executed by a processor of the server computing device receives a URL from a client agent application executing on a client computing device. At 406, responsive to determining, based upon the URL, that the graphical resource is to be provided by a third-party application, the server agent application causes an intermediate application to be launched on the server computing device. At 408, the intermediate application requests a webpage from the third-party application. The webpage includes a security token for a user session between the client agent application and the third-party application. At 410, responsive to receiving the webpage, the intermediate application extracts the security token from the webpage. At 412, the intermediate application constructs a modified URL based upon the URL and the security token. At 414, the intermediate application transmits the modified URL to the third-party application, wherein the third-party application causes the graphical resource to be presented on a display. The methodology 400 concludes at 416.

Turning now to FIG. 5, a methodology 500 performed by a client computing device that facilitates CSRF attack protection is illustrated. The methodology 500 begins at 502, and at 504, the client computing device receives a selection of a graphical object shown on a display, the graphical object assigned to a graphical resource that is to be provided by a third-party application. At 506, the client computing device constructs a URL based upon the identifier for the graphical resource. At 508, the client computing device transmits the URL to a server agent application. At 510, the client computing device receives the graphical resource from the server agent application via an intermediate application. At 512, the client computing device presents the graphical resource on the display. The methodology 500 concludes at 514.

While the above-described technologies have been described in a healthcare context, it is to be appreciated that the above-described technologies may be applied in other contexts. For instance, the above-described technologies may be used in a financial context when a financial application requests graphical resources from a third-party application, but cannot expose a security token to a user within a URL for security reasons. Moreover, while the intermediate application 142 has been described as executing on the second server computing device 134, it is to be understood that the intermediate application 142 may be a web server that executes on the second server computing device 134 or another server computing device.

Figure 6:
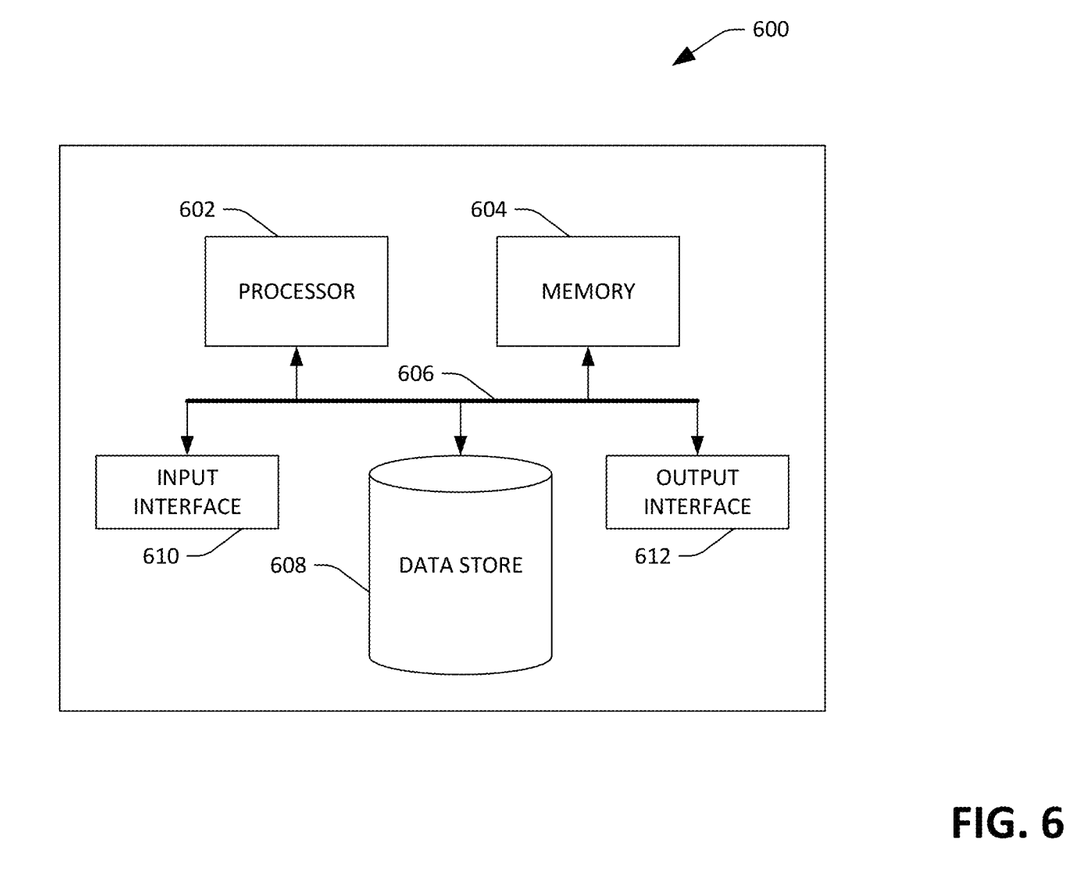
FIG. 6 is an exemplary computing system.

Referring now to FIG. 6, a high-level illustration of an exemplary computing device 600 that can be used in accordance with the systems and methodologies disclosed herein is illustrated. For instance, the computing device 600 may be used in a system that protects against CSRF attacks. By way of another example, the computing device 600 can be used in a system that generates GUI features for an agent application. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store patient data, graphical features, etc.

The computing device 600 additionally includes a data store 608 that is accessible by the processor 602 by way of the system bus 606. The data store 608 may include executable instructions, patient data, graphical features, etc. The computing device 600 also includes an input interface 610 that allows external devices to communicate with the computing device 600. For instance, the input interface 610 may be used to receive instructions from an external computer device, from a user, etc. The computing device 600 also includes an output interface 612 that interfaces the computing device 600 with one or more external devices. For example, the computing device 600 may display text, images, etc. by way of the output interface 612.

It is contemplated that the external devices that communicate with the computing device 600 via the input interface 610 and the output interface 612 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 600 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 600 may be a distributed system. Thus, for instance, several devices may be in communication by way of a network connection and may collectively perform tasks described as being performed by the computing device 600.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device, comprising:
   a processor; and
   memory storing instructions that, when executed by the processor, cause the processor to perform acts comprising:
   receiving, by a server agent application being executed by the processor, a uniform resource locator (URL) from a client agent application executing on a client computing device, the URL including an identifier for a graphical resource that is to be provided by a third-party application;
   responsive to determining, by the server agent application and based upon the URL, that the graphical resource is to be provided by the third-party application, causing, by the server agent application, an intermediate application to be launched that is executed by the processor;
   requesting, by the intermediate application, a webpage from the third-party application, the webpage including a security token for a user session between the client agent application and the third-party application;
   responsive to receiving the webpage from the third-party application, extracting, by the intermediate application, the security token from the webpage;
   constructing, by the intermediate application, a modified URL based upon the URL and the security token;
   transmitting, by the intermediate application, the modified URL to the third-party application, wherein the third-party application generates the graphical resource based upon the modified URL;

receiving, by the intermediate application, the graphical resource;

removing, by the intermediate application, the security token from the graphical resource; and transmitting, by the intermediate application, the graphical resource to the client agent application, wherein the client agent application presents the graphical resource on a display of the client computing device.

2. The server computing device of claim 1, wherein the client agent application causes credentials for a user of the client agent application to be transmitted to the third-party application prior to the server computing device receiving the URL from the client agent application, wherein the third-party application generates the security token responsive to authenticating the credentials for the user.

3. The server computing device of claim 1, wherein the client agent application displays a source view, wherein the graphical resource is a target view, wherein the client agent application receives a selection of a graphical object shown within the source view, thereby causing the URL to be received by the server agent application, wherein the URL further includes an identifier for the source view.

4. The server computing device of claim 1, wherein the third-party application authenticates the user based upon the security token included in the modified URL.

5. The server computing device of claim 4, wherein intermediate application ceases execution subsequent to transmitting the graphical resource to the client agent application.

6. The server computing device of claim 1, wherein the graphical resource is a graphical user interface (GUI), the acts further comprising:

retrieving, by the server agent application, patient data for a patient based upon an identifier for a patient received by the server agent application; and transmitting, by the server agent application, the patient data to the client agent application, wherein the client agent application populates the GUI with the patient data.

7. The server computing device of claim 1, the acts further comprising:

receiving, by the server agent application, a second URL from the client agent application, the second URL including an identifier for a second graphical resource that is to be provided by the third-party application;

responsive to determining, by the server agent application and based upon the second URL, that the second graphical resource is to be provided by the third-party application, causing, by the server agent application, the intermediate application to be launched;

requesting, by the intermediate application, a second webpage from the third-party application, the second webpage including the security token for the user session between the client agent application and the third-party application;

responsive to receiving the second webpage from the third-party application, extracting, by the intermediate application, the security token from the second webpage;

constructing, by the intermediate application, a second modified URL based upon the second URL and the security token; and transmitting, by the intermediate application, the second modified URL to the third-party application, wherein the third-party application generates the second graphical resource based upon the second modified URL, wherein the third-party application causes the second graphical resource to be presented on the display of the client computing device.

8. The server computing device of claim 1, wherein the client agent application is executed within a web browser executed the client computing device.

9. The server computing device of claim 1, the acts further comprising:

prior to the intermediate application requesting the webpage and subsequent to the server agent application causing the intermediate application to be launched, causing, by the server agent application, the URL to be provided to the intermediate application.

10. The server computing device of claim 1, wherein the client computing device further executes a client electronic health records (EHR) application, wherein the client EHR application communicates with a server EHR application executing on a second server computing device in order to facilitate care of patients in a healthcare facility, wherein a graphical user interface (GUI) for the agent application is displayed concurrently on the display with a GUI for the client EHR application, wherein the graphical resource is incorporated into the GUI for the client agent application.

11. The server computing device of claim 1, wherein the third-party application is a business intelligence application.

12. A method executed by a processor of a server computing device, comprising:

receiving, by a server agent application being executed by the processor, a uniform resource locator (URL) from a client agent application executing on a client computing device, the URL including an identifier for a graphical resource that is to be provided by a third-party application;

responsive to determining, by the server agent application and based upon the URL, that the graphical resource is to be provided by the third-party application, causing, by the server agent application, an intermediate application to be launched that is executed by the processor;

requesting, by the intermediate application, a webpage from the third-party application, the webpage including a security token for a user session between the client agent application and the third-party application;

responsive to receiving the webpage from the third-party application, extracting, by the intermediate application, the security token from the webpage;

constructing, by the intermediate application, a modified URL based upon the URL and the security token;

transmitting, by the intermediate application, the modified URL to the third-party application, wherein the third-party application generates the graphical resource based upon the modified URL;

receiving, by the intermediate application, the graphical resource;

removing, by the intermediate application, the security token from the graphical resource; and transmitting, by the intermediate application, the graphical resource to the client agent application, wherein the client agent application presents the graphical resource on a display of the client computing device.

13. The method of claim 12, wherein the client agent application causes credentials for a user of the client agent application to be transmitted to the third-party application prior to the server computing device receiving the URL from the client agent application, wherein the third-party application generates the security token responsive to authenticating the credentials for the user.

14. The method of claim 12, further comprising:
receiving, by the server agent application, a second URL from the client agent application, the second URL including an identifier for a second graphical resource that is to be provided by the third-party application;
responsive to determining, by the server agent application and based upon the second URL, that the second graphical resource is to be provided by the third-party application, causing, by the server agent application, the intermediate application to be launched;
requesting, by the intermediate application, a second webpage from the third-party application, the second webpage including the security token for the user session between the client agent application and the third-party application;
responsive to receiving the second webpage from the third-party application, extracting, by the intermediate application, the security token from the second webpage;
constructing, by the intermediate application, a second modified URL based upon the second URL and the security token; and
transmitting, by the intermediate application, the second modified URL to the third-party application, wherein the third-party application generates the second graphical resource based upon the second modified URL, wherein the third-party application causes the second graphical resource to be presented on the display of the client computing device.

15. The method of claim 12, wherein the graphical resource is comprised by Hypertext Markup Language (HTML) code.

16. The method of claim 12, wherein the security token is a random number or a pseudo-random number.

17. The method of claim 12, wherein the intermediate application ceases execution subsequent to the graphical resource being presented on the display of the client computing device.

18. A non-transitory computer-readable storage medium comprising instructions that, when executed by a processor of a client computing device, cause the processor to perform acts comprising:

receiving, by a server agent application being executed by the processor, a uniform resource locator (URL) from a client agent application executing on a client computing device, the URL including an identifier for a graphical resource that is to be provided by a third-party application;
responsive to determining, by the server agent application and based upon the URL, that the graphical resource is to be provided by the third-party application, causing, by the server agent application, an intermediate application to be launched that is executed by the processor;
requesting, by the intermediate application, a webpage from the third-party application, the webpage including a security token for a user session between the client agent application and the third-party application;
responsive to receiving the webpage from the third-party application, extracting, by the intermediate application, the security token from the webpage;
constructing, by the intermediate application, a modified URL based upon the URL and the security token;
transmitting, by the intermediate application, the modified URL to the third-party application, wherein the third-party application retrieves the graphical resource based upon the modified URL;
receiving, by the intermediate application, the graphical resource;
removing, by the intermediate application, the security token from the graphical resource; and
transmitting, by the intermediate application, the graphical resource to the client agent application, wherein the client agent application presents the graphical resource on a display of the client computing device.

19. The non-transitory computer-readable storage medium of claim 18, wherein the graphical resource is a graphical user interface (GUI), the acts further comprising:
retrieving, by the server agent application, patient data for a plurality of patients based upon a patient characteristic received by the server agent application; and
transmitting the patient data to the client agent application, wherein the client agent application populates the GUI with the patient data.

* * * * *